United States Patent
Thornton

(10) Patent No.: US 9,389,164 B2
(45) Date of Patent: Jul. 12, 2016

(54) METHODS OF AND APPARATUS FOR MEASURING METAL CLEANLINESS

(71) Applicant: NOVELIS INC., Atlanta, GA (US)

(72) Inventor: Gary Thornton, Fort Collins, CO (US)

(73) Assignee: Novelis Inc., Atlanta, GA (US)

( * ) Notice: Subject to any disclaimer, the term of this patent is extended or adjusted under 35 U.S.C. 154(b) by 69 days.

(21) Appl. No.: 14/203,257

(22) Filed: Mar. 10, 2014

(65) Prior Publication Data

US 2014/0266150 A1 Sep. 18, 2014

Related U.S. Application Data

(60) Provisional application No. 61/778,028, filed on Mar. 12, 2013.

(51) Int. Cl.

| | |
|---|---|
| G01N 27/00 | (2006.01) |
| G01N 15/06 | (2006.01) |
| G01N 33/20 | (2006.01) |
| G01N 15/00 | (2006.01) |
| G01N 27/06 | (2006.01) |

(52) U.S. Cl.
CPC .......... *G01N 15/0656* (2013.01); *G01N 33/206* (2013.01); *G01N 27/06* (2013.01); *G01N 2015/0053* (2013.01)

(58) Field of Classification Search
CPC ....... G01N 27/00; G01N 27/02; G01N 27/06; G01N 27/22; G01N 27/221; G01N 27/226; G01N 15/00; G01N 15/06; G01N 15/0656; G01N 33/20; G01N 33/203; G01N 33/206; G01N 2015/0053; G01N 2015/0057; G01R 27/22

USPC ............... 324/71.1, 71.4, 720, 444, 442, 613, 324/693; 377/10–12; 266/78, 80, 81, 99; 73/1.02, 865.9, 866; 164/4.1

See application file for complete search history.

(56) References Cited

U.S. PATENT DOCUMENTS

| | | | |
|---|---|---|---|
| 3,389,335 A | 6/1968 | Anthony et al. | |
| 4,450,435 A * | 5/1984 | James | 340/511 |

(Continued)

OTHER PUBLICATIONS

International Patent Application No. PCT/US2014/022822, International Search Report and Written Opinion mailed Aug. 14, 2014, 9 pages.

(Continued)

*Primary Examiner* — Arleen M Vazquez
*Assistant Examiner* — Steven Yeninas
(74) *Attorney, Agent, or Firm* — Kilpatrick Townsend & Stockton LLP

(57) ABSTRACT

Methods and apparatus for measuring the cleanliness of molten metals. Direct current is passed between electrodes through molten metal advancing through a passage in an electrically resistive wall. A voltage signal is analyzed for the presence of solid generally non-metallic inclusions in the metal. Direct current is supplied by one or more ultra-capacitors and the decay in discharge voltage of the capacitor(s) is compensated for by passing the current from each capacitor through a resistor ladder network circuit having resistors connected in parallel. Individual resistors are switched on or off in a sequence effective to change the resistance of the circuit and maintain the current within a predetermined range. Heat generation and noise pick-up are minimized by maintaining a low discharge voltage and measurement current while using FETs only in the fully ON or OFF conditions to switch the resistors into or out of the circuits.

24 Claims, 2 Drawing Sheets

(56) References Cited

U.S. PATENT DOCUMENTS

| | | | |
|---|---|---|---|
| 4,555,662 | A | 11/1985 | Doutre et al. |
| 4,600,880 | A | 7/1986 | Doutre et al. |
| 4,775,833 | A | 10/1988 | Roos et al. |
| 4,810,911 | A | 3/1989 | Noguchi |
| 5,039,935 | A * | 8/1991 | Hachey et al. ............... 324/71.4 |
| 5,130,639 | A * | 7/1992 | Hachey ........................ 324/71.4 |
| 5,130,883 | A * | 7/1992 | Edwards ....................... 361/91.1 |
| 5,896,113 | A * | 4/1999 | O'Neill, Jr. .................... 343/895 |
| 7,459,896 | B2 | 12/2008 | Marcotte et al. |
| 7,466,156 | B2 * | 12/2008 | Marsh et al. ............... 324/750.3 |
| 7,752,953 | B2 | 7/2010 | Sokol et al. |
| 7,780,906 | B2 | 8/2010 | Burty et al. |
| 7,972,950 | B2 | 7/2011 | Na et al. |
| 2001/0005130 | A1 | 6/2001 | Manzini et al. |
| 2002/0067155 | A1 * | 6/2002 | Conti ..................... G01N 1/125 324/71.4 |
| 2004/0201371 | A1 * | 10/2004 | Conti ................. G01N 15/1031 324/71.1 |
| 2005/0231185 | A1 * | 10/2005 | Marcotte et al. ............. 324/71.1 |

OTHER PUBLICATIONS

Draganovici, "A user-friendly software interface for the liquid metal cleanliness analyzer (LiMCA)," Thesis, 1994, Canada/McGill University, 4 pages.

Carozza, "Water Modelling of Particle Discrimination Using LiMCA Technology," Thesis, Sep. 1999, Canada/McGill University, 12 pages.

Jung, Do Yang, "Shield Ultracapacitor Strings From Overvoltage Yet Maintain Efficiency," Electronic Design, May 27, 2002, http://electronicdesign.com/components/shield-ultracapacitor-strings-overvoltage-yet-maintain-efficiency, Penton Media, Inc., 3 pages.

Miller, John M., et al., "Carbon-Carbon Ultracapacitor Equivalent Circuit Model, Parameter Extraction, and Application", Slide 39, Oct. 18, 2007, Ansoft Ansoft Frist Pass Workshop, Southfield, Michigan, 2 pages.

"IRF1324S-7PPbF HEXFET Power MOSFET," Specifications Datasheet, Dec. 21, 2010, International Rectifier, El Segundo, California, 9 pages.

Badowski et al., "Measurement of Non-Metallic Inclusions in the Size Range of 10-20 μm by LiMCA," Light Metals 2012, 2012, pp. 1077-1083, TMS (The Mineral, Metals & Materials Society), 7 pages.

Autosignal, "Cutting Edge Signal Analysis Software," 2013, http://www.sigmaplot.com/products/autosignal/autosignal.php, AutoSignal: Cutting Edge Signal Analysis Software by Systat Software, 2 pages.

International Patent Application No. PCT/US2014/022768, International Search Report and Written Opinion mailed Jun. 3, 2014, 11 pages.

* cited by examiner

METHODS OF AND APPARATUS FOR MEASURING METAL CLEANLINESS

RELATED APPLICATION

This application claims the benefit of U.S. Provisional Patent Application Ser. No. 61/778,028 filed Mar. 12, 2013, the entire contents of which are incorporated by reference.

FIELD OF THE INVENTION

This invention relates to methods of and apparatus for measuring the cleanliness of molten metals, i.e. the presence or absence of solid, generally non-metallic, inclusions within the molten metal.

BACKGROUND OF THE INVENTION

Molten metals, particularly molten aluminum and molten steel, are frequently contaminated by entrained small non-metallic inclusions that give rise to a variety of shortcomings or defects in products manufactured from the molten metal. For example, such inclusions may cause the solidified metal to tear during mechanical working operations, or may introduce pin-holes and streaks in foils and surface defects and blisters into sheets, or give rise to increased rates of breakage during the production of metal wire, etc.

A known analyzer that enables quick measurements of metal cleanliness and provides size and concentration information of the inclusions is the so-called Liquid Metal Cleanliness Analyzer (often abbreviated to "LiMCA"). A conventional LiMCA apparatus may comprise a probe having an electrically-insulating wall means, often in the form of a sampling tube, having a small precisely-dimensioned passage in a side wall. The tube is immersed in the molten metal to be tested and a uniform stream of the metal is drawn by vacuum or pressure through the small passage while a substantially constant electric current is passed through the stream between electrodes disposed respectively inside and outside the tube. The particulate inclusions generally have very high electrical resistivity compared to the molten metal, and the travel of a particle through the passage is accompanied by a change in resistance for the electric current within the passage, thereby producing an electrical pulse in the voltage across the electrodes. The number of pulses produced while a fixed volume of metal transits the passage provides an indication of the number of particles per unit volume present within the metal. Furthermore, it is possible to analyze the pulse to determine particle size and size distribution. Generally, the voltage is monitored in real time, but the voltage trace may be recorded and analyzed afterwards and kept for future referral. Examples of typical LiMCA devices are described in U.S. Pat. Nos. 4,600,880, 5,130,639, 4,555,662, and 5,039,935.

For LiMCA apparatus to work effectively, the current flowing between the electrodes must be direct current (DC) and must be kept fairly constant for a sufficient period of time, e.g. 30 seconds or so, to allow for a reliable measurement. Also, the current passing between the electrodes must be kept fairly high, and it is desirable to minimize random electrical noise that can undesirably obscure the desired voltage signal. To meet these requirements, it has been usual to provide the apparatus with one or more rechargeable batteries (for example of the Nickel-Cadmium type), to generate the required DC current during the testing phase. The batteries are recharged between the test cycles when the generation of electrical noise is not important, e.g. using a mains generator or battery recharger. While the use of batteries as the current source can be effective, batteries take a significant time to recharge and require additional equipment to ensure that the recharging takes place properly. They also tend to be heavy, bulky and may have a short operational life if constantly subjected to rapid discharge and recharge cycles Another problem that conventional apparatus may encounter is the generation of considerable heat, representing a loss of efficiency and requiring extra size and weight for cooling devices or heat sinks. The use of ultra-capacitors, rather than batteries, as power sources for LiMCA devices has been disclosed in U.S. Pat. No. 7,459,896 which issued to Marcotte et al. on Dec. 2, 2008 ("the Marcotte et al. patent") (the disclosure of which patent is specifically incorporated herein by this reference). As explained in this patent, ultra-capacitors can be employed as power sources as an alternative to rechargeable batteries. However, ultra-capacitors have a lower volume charge density than rechargeable batteries and cannot therefore supply high currents at constant rates for extended periods of time. In the device of the Marcotte et al. patent, the use of an ultra-capacitor can result in the generation of significant heat and require circuitry that is susceptible to inclusion of electrical noise. This has necessitated complex measures for eliminating noise from the test signal, e.g. by providing three or more electrodes to generate a reference signal for comparison purposes. There is therefore a desire for alternative approaches that enable the use of ultra-capacitors as a current source without attendant disadvantages.

Previous LiMCA designs, particularly those incorporating batteries, have generally employed large ballast resistors and transistors operating in a linear (intermediate) region to maintain a steady current generating high heat losses and requiring heat management to keep operating temperatures within a safe region. There is therefore a need for alternative designs and methods of use of LiMCA equipment.

SUMMARY OF THE INVENTION

One exemplary embodiment of the present invention provides apparatus for measuring cleanliness of a molten metal. The apparatus comprises one or more rechargeable ultra-capacitors operable at a discharge voltage of 2.7 volts or less, at least two electrodes, and a metal cleanliness probe having an interior, a wall made of electrically resistive material and a passage in the wall interconnecting the interior with an exterior of the probe to allow molten metal to pass therethrough. One of the at least two electrodes is positioned in the interior of the probe as an interior electrode and another of the at least two electrodes is positioned outside the probe as an exterior electrode. A device is provided registering voltage across the interior and exterior electrodes and generating a voltage signal. For the or for each of the one or more ultra-capacitors, an associated resistor ladder network circuit is provided interconnecting its associated ultra-capacitor with one of the electrodes. The or each resistor ladder network circuit comprises two or more resistors connected in parallel to each other, each resistor being in a circuit leg including one or more field effect transistors capable of being switched directly between a non-conductive OFF condition and a fully conductive ON condition. The resistor ladder network circuit or circuits have resistance values effective to maintain a measurement current of no more than 100 amps through molten metal present in the passage when the circuit or circuits are exposed to the discharge voltage from the one or more ultra-capacitors. A controller is provided adapted for individually switching the field effect transistors of the circuit legs of the or each resistor ladder network circuit between the non-conductive OFF condition and the fully conductive ON condition according to a sequence effective for maintaining the measurement current within a pre-determined current range at least for a time required for measurement of cleanliness of the molten metal.

There may be a single ultra-capacitor and associated resistor ladder network circuit, but alternatively there may be two or more such ultra-capacitors and circuits to reduce the current carried by each resistor circuit, although it will be recognized that the "footprint" of the apparatus required when two, or more especially more than two, of such ultra-capacitors and circuits are provided likely increases the size and cost of the apparatus.

In one exemplary form, the field effect transistor or transistors of each or most of the circuit legs are surface mounted field effect transistors that employ minimum space in the apparatus and avoid undue susceptibility to noise. Such FETs have component bodies that are directly attached to an underlying circuit board and have projecting terminals that are connected to the circuit paths of the circuit board without requiring the presence of holes in the circuit board. Such FETs may have very low resistance in the fully conductive ON condition and, when subjected to relatively low voltages (i.e. 2.7 volts, and alternatively 1.4 volts, or less) in a resistor ladder network circuit, generate little heat, so there is usually no need to provide the FETs with bulky and heavy heat sinks conventionally used for FETs of other kinds. Moreover, by mounting the FETs directly onto the circuit board, the use of elongated leads is not required, and this reduces the amount of random noise picked up by the devices since such leads act as small antennas. In exemplary embodiments, the FETs are switched directly from nonconductive OFF condition to the fully-conductive ON condition in a very short period of time (e.g. typically less than 1 µs). Suitable FETs of this kind may be obtained, for example, from International Rectifier of El Segundo, Calif. 90245, USA, or Digi-Key Corporation of Thief River Falls, Minn. 56701, USA.

In one exemplary embodiment, the field effect transistor or transistors of each of the circuit legs may be chosen to introduce a resistance of less than 1 milli-ohm into the circuit leg when in the fully conductive ON condition, thus minimizing heat loss in the circuit. Such minimal resistance values may also be achieved by providing two or more field effect transistors connected in parallel in a circuit leg, thereby reducing the combined resistance introduced by the field effect transistors into the circuit leg. This allows the use of field effect transistors that may have a higher resistance in the ON condition than would be desired for individual use.

The use of surface-mounted FETs enables the design to be made compact, and the compact circuitry reduces noise in the voltage signal that makes it possible to determine the metal cleanliness from the voltage signal while employing only two electrodes, i.e. without having to provide additional electrodes and circuitry for noise-elimination purposes.

A particular exemplary embodiment employs two ultra-capacitors and two separate resistor ladder network circuits. This reduces the current flow in each network circuit to half what it would have been if using a single ultra-capacitor and a single resistor ladder network circuit. This allows each circuit to stay cooler during the measurement period. Each ultra-capacitor then provides half of the current required. For example, if the apparatus requires a measurement current of 60-65 amps, each ultra-capacitor and resistor ladder network circuit would provide 30-32.5 amps, each circuit being connected to the electrodes to provide current flow in the same direction. Of course, more than two ultra-capacitors and resistor network circuits could be employed in this way, but with a consequent need for additional capital and size requirements.

The resistors of the or each resistor ladder network circuit may have resistance values that differ from each other. The controller may then be programmed to switch the field effect transistors of the circuit legs to first turn on a circuit leg of lowest resistance, and then to turn on one or more circuit legs of higher resistance as the discharge voltage of the associated ultra-capacitor declines during the time required for measurement. When there are three or more circuit legs per resistor ladder network circuit, the controller may be programmed to turn on the circuit legs according to a binary sequence effective to maintain the measurement current within the pre-determined current range.

The resistors employed in the resistor ladder network may individually be of low resistance values for example, in one exemplary embodiment, within a range of 0.02 to 2.64 ohms, or alternatively within a range of 0.02 to 0.66 ohms.

The apparatus may further include a device for measuring the measurement current and for generating a signal alerting the controller when the current falls to a lower limit of the pre-determined current range, so that the controller can then switch FETs on and/or off to maintain the measurement current within the pre-determined range. The apparatus may also include a voltage signal analyzer adapted to determine metal cleanliness from the signal from the device registering voltage, and one or more chargers for charging the ultra-capacitor(s) between metal cleanliness measurements.

The apparatus in one exemplary embodiment may include circuitry for purging the passageway of debris and scale prior to cleanliness measurements. In one form, this may take the form of a switchable circuit by-passing the resistor ladder network circuit and connecting the or each ultra-capacitor in parallel directly across the interior and 5 exterior electrode for purging the passage. For higher purging currents, the apparatus may include a switchable circuit connecting two or more ultra-capacitors in series and by-passing the resistor ladder network circuits to connect the series-connected ultra-capacitors across the interior and exterior electrodes. The higher voltage of the series-connected ultra-capacitors produces a higher current through the passage than an alternative form in which two or more ultra-capacitors are connected in parallel.

In one exemplary form, the apparatus may employ two, and no more than two, electrodes, i.e. a single internal electrode and a single external electrode. This is because the resistance of the exemplary apparatus to noise pick-up may enable the resulting voltage signal to be analyzed without elaborate noise-cancellation equipment. The resistance to noise may be improved in particular by positioning the resistors and surface mounted field effect transistors on the same circuit board immediately adjacent to each other, thereby minimizing the footprint of the circuit components and the lengths of connectors. A combination of features also makes it possible to largely avoid the presence of heat sinks conventionally used to withdraw heat from resistors and field effect transistors because these elements may run quite cool (e.g. cool enough to touch). This is possible because of one or more features, such as a low discharge voltage of the ultra-capacitors, a low resistance of the field effect transistors in the ON condition, a relatively low measurement current, low resistance values of the resistors, etc., as discussed.

Another exemplary embodiment of the invention provides a method of measuring cleanliness of a molten metal. The method comprises charging at least one ultra-capacitor to an initial discharge voltage of 2.7 volts or less (e.g. to a voltage of 1.4 volts or less, for example in the range of about 0.8 to 1.4 volts), advancing molten metal through a passage in a wall made of electrically resistive material between an interior and an exterior of a metal cleanliness probe, discharging the at least one ultra-capacitor, via a resistor ladder network circuit associated with the or each ultra-capacitor, through the molten metal advancing through the passage between an interior electrode positioned in the interior of the probe and an exterior electrode positioned outside the probe, registering voltage across the internal and external electrodes during the time required for measurement, generating a voltage signal and determining cleanliness of the molten metal from the voltage signal. The or each resistor ladder network circuit (when there is more than one) comprises two or more resistors connected in parallel to each other, each resistor being in a circuit leg including one or more field effect transistors capable of being switched directly between a non-conductive OFF condition and a fully conductive ON condition, the resistor ladder network having resistance values effective to maintain a measurement current of no more than 100 amps (e.g. about 55 to 65 amps, or about 60 to 65 amps) through the molten metal advancing through the passage. The field effect transistors of the circuit legs of the or each resistor ladder network circuit are switched on or off between the non-conductive OFF condition and the fully conductive ON condition according to a sequence for maintaining the measurement current within a pre-determined current range for at least a time required for measurement of cleanliness of the molten metal.

In one exemplary form, each resistor ladder network circuit has three or more circuit legs (generally up to six) and the individual switching of the field effect transistors of the circuit legs of the or each resistor ladder network ladder circuit is carried out according to a binary sequence to maintain the measurement current within the pre-determined current range. The sequence may be pre-determined according to a calibration routine and recorded for use during the time required for measurement of cleanliness of the molten metal. In one form, the field effect transistors are switched from the OFF to the ON condition by voltage signals generated by a controller, e.g. an electronic circuit containing a micro-processor and optionally a memory device and timer.

If desired, the passage may be purged before the time required for measurement of cleanliness of the molten metal by directing current from the at least one ultra-capacitor through molten metal in the passage while causing the current to by-pass the or each resistor ladder network circuit. In one exemplary form, two or more of the ultra-capacitors are connected in series so that an increased voltage may be applied across the electrodes as the series-connected ultra-capacitors are discharged through the passage.

Exemplary apparatus embodiments of the invention may be made quite compact because heat generation is kept to a minimum by limiting the operational voltage of the ultra-capacitor to no more than 2.7 volts (e.g. less than 1.4 volts, such as within a range of 0.8 to 1.4 volts), by limiting the measurement current to no more than 100 amps, and by employing FETs that have low resistance when in the fully conductive ON conditions, e.g. no more than a few milli-ohms and, for example, no more than 1 milli-ohm. As noted above, FETs with higher resistance may be employed with the same effect if two or more are connected in parallel within a leg of the circuit.

In exemplary embodiments, the resistor ladder circuit network provides a way of employing FETs without resorting to operation of such devices in their intermediate ranges that generate significant heat. Thus, the devices may be used only the nonconductive OFF condition and the fully conductive ON condition that generate almost no losses. There is then very little heat generated by the FETs or the resistors and the need for bulky and heavy heat sinks can be avoided. As previously noted, this also makes it possible to use surface mounted FETs, which take up less space and are less susceptible to reception of electrical noise.

By adjusting ladder resistor values, ultra-capacitor charge voltage, calibration parameters, and/or control set points (e.g. via firmware), exemplary embodiments can be adjusted for sampling in different metals and can be adjusted for higher or lower discharge currents and tighter or looser current ripple (i.e. range between maximum and minimum currents during sampling).

BRIEF DESCRIPTION OF THE DRAWINGS

Exemplary embodiments of the present invention are described in detail below in conjunction with the accompanying drawings, in which.

DETAILED DESCRIPTION

Figure 1:
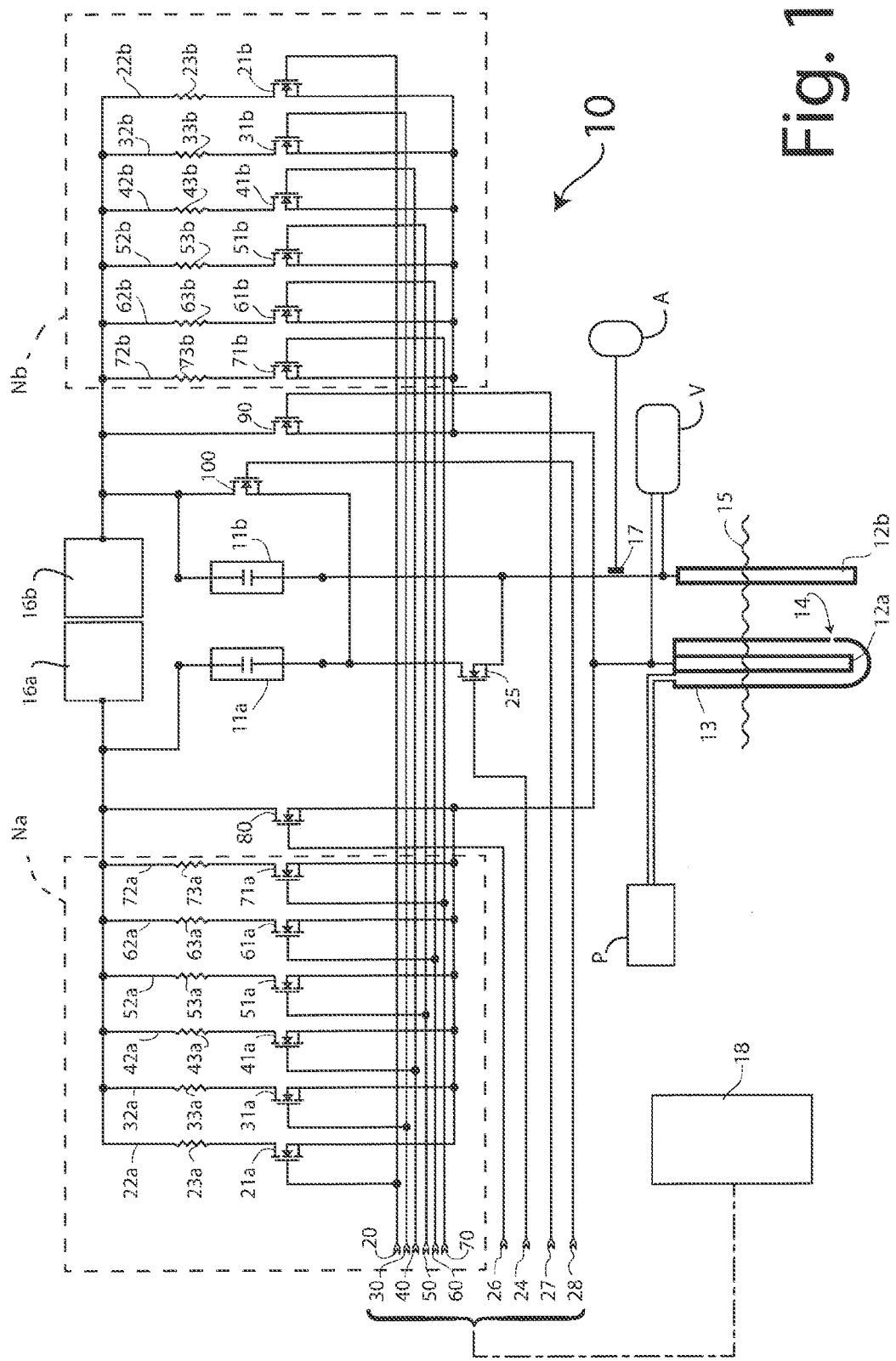
FIG. 1 is a combined circuit diagram and schematic sketch illustrating an exemplary embodiment of the present invention.

FIG. 1 shows a circuit diagram suitable for supplying cleanliness-measurement current in a LiMCA analyzer according to one exemplary embodiment of the invention. This circuit, or at least the majority of it, may be provided on a circuit board referred to as a "power board." The apparatus may also include a "main board" containing equipment for initiating a calibration routine, and an "analog board" containing measuring, recording and possibly signal processing devices. For convenience, the main board may be remote from the power board and analog board, e.g. located in a control case (not shown) connected to the power board in a probe unit by an umbilical cable of suitable length (for example, thirty feet in length). The analog board is preferably positioned as close as possible to the power board for minimal susceptibility to noise.

In the circuit diagram 10, two ultra-capacitors 11a and 11b are provided to supply direct current ultimately to electrodes 12a (positive) and 12b (negative) during a measurement period of the apparatus. The electrodes are positioned on opposite sides of a wall of an enclosed hollow tubular probe 13 made of electrically resistive material having a small passage 14 therein such that the electrode 12a is internal of the probe and electrode 12b is external of the probe. The probe 13 and the external electrode 12b are immersed in molten metal to be analyzed (represented by wavy surface line 15). Before the measurement period begins, the ultra-capacitors 11a and 11b are each charged by associated charging devices 16a and 16b up to a voltage at which they are capable, together, of delivering a predetermined measurement current, in one embodiment at least 65 amps, but no more than 100 amps, when the measurement period begins. The maximum charging voltage is kept low compared voltages at which ultra-capacitors normally operate, e.g. a maximum of 2.7 volts and generally in the range of 0.8 to 1.4 volts. The charging devices 16a, 16b and accompanying circuitry are turned off before and at all times during the measurement period to prevent electrical noise generation from AC circuits and the like used by such devices. The use of such low voltages contributes to the desired low heat losses.

The positive terminals of the ultra-capacitors 11a and 11b are each connected to the internal electrode 12a via separate resistor ladder network circuits Na and Nb switchable by field effect transistors (FETs), all of which are of the surface mounted type to allow for a compact design (i.e. they are mounted in direct contact with a supporting circuit board). The negative terminals of both ultra-capacitors 16a, 16b are connected to electrode 12b when FET 25 is turned on.

To commence a measurement operation, a vacuum pump P (or alternatively a vacuum reservoir) withdraws air from the interior of the probe 13 and the resultant vacuum draws molten metal at a constant rate into the probe interior through the narrow passage 14. A control voltage is applied through line 20 to FETs 21a and 21b to turn on the circuits 22a and 22b (referred to as circuit "legs" of the resistor ladder network circuits) leading from the positive terminals of the ultra-capacitors 11a and 11b, respectively, thereby allowing connection to the positive electrode 12a. The circuit legs 22a and 22b contain ballast resistors 23a and 23b, respectively, of the same resistance value suitable for allowing a combined current through the metal of no more than 100 amps, and preferably 65 to 70 amps. At the same time, a control voltage is applied via line 24 to FET 25 to turn on the FET and thus connect the negative terminal of ultra-capacitor 11a to the negative electrode 12b to complete the circuit. The negative electrode of ultra-capacitor 11b is constantly connected to the negative electrode 12b, so at this stage both ultra-capacitors supply current through the metal in passage 14 via the electrodes 12a and 12b. As the current flows through the metal, the voltage across the electrodes is measured by a device registering voltage and producing a voltage signal, e.g. a voltage recording and analyzing apparatus V, so that the presence and characteristics of pulses in the voltage signal that are characteristic of metal inclusions can be detected, measured, assessed and determined.

As the testing operation proceeds, the output voltages of the ultra-capacitors 11a and 11b rapidly decay, so the current passing through the metal in passage 14, measured for example by a current-measuring device 17 (e.g. a Hall-effect transducer) and viewed or recorded by current meter A, starts to decline from the desired initial value of 65-70 amps. To compensate for this decline, and to maintain the current in a predetermined measurement range of, for example, approximately 60 to 65 A, one or more additional ladder network "legs" 32a/32b, 42a/42b, 52a/52b, 62a/62b and 72a/72b of the ladder network circuits are activated (on), so that current may flow respectively through resistor pairs 33a/33b, 43a/43b, 53a/53b, 63a/63b and/or 73a/73b to reduce the overall resistance in the ladder network circuits between the ultra-capacitors and the internal electrode 12a. This is achieved by applying control voltages via lines 30, 40, 50, 60 and 70 as required to FET pairs 31a/31b, 41a/41b, 51a/51b, 61a/61b and 71a/71b, respectively. The application of such control voltages is under the control of a FET controller 18 which may comprise a micro-processor device.

The sequence in which such FETs are turned on is chosen to maintain the measurement current always within the desired range, e.g. approximately 55 to 65 amps, or alternatively approximately 60 to 65 amps, as the voltage of the ultra-capacitors 11a, 11b decays. In a particular example of the illustrated circuit, if resistors 23a/23b are each said to have a resistance value of "R", resistors 33a/33b preferably each have a resistance value of 2×R, resistors 43a/43b preferably each have resistance value of 4×R, resistors 53a/53b preferably each have a resistance value of 8×R, resistors 63a/63b preferably each have a resistance value of 16×R and resistors 73a/73b preferably each have a resistance value of 32×R. In such a circuit intended for use with molten aluminum or aluminum alloys, the R value may be 0.020 ohm with the resistances of the various resistors thus being:

23a/23b=0.020 ohm
33a/33b=4×0.15 ohm in parallel=0.0375 ohm
43a/43b=2×0.15 ohm in parallel=0.075 ohm
53a/53b=0.15 ohm
63a/63b=0.33 ohm; and
73a/73b=2×0.33 ohm in series=0.66 ohm.

In an exemplary control sequence, resistors 23a/23b are turned on first. Then, as the voltage decays, additional resistors are turned on as needed according to a binary coded sequence starting with resistors 73a/73b which produces the smallest current change. Then resistors 73a/73b are turned off and resistors 63a/63b are turned on causing twice the current change that resistors 73a/73b did. Then both resistors 73a/73b and 63a/63b are turned on, and so forth in a binary sequence, i.e. 100000, 100001, 100010, 100011, 100100, 100101, 100110, . . . 111111 (i.e. 32 states in all), where the least significant digit controls resistors 73a/73b and the most significant digit controls resistors 23a/23b. This sequence of 32 resistor transitions are brought successively into use as the current drops to around 60 amps to maintain the measurement current within the desired range. In fact, only some of the 32 states 100001 to 111111 may be effective to maintain the current value, and normally at least 5 or 6 states are effective. By switching to these states, the current flow through the metal in the passage 14 can be kept within a desired range of e.g. 60 to 65 amps during the time required for a measurement of metal cleanliness (usually at least 30 seconds) despite the rapid voltage decay of the ultra-capacitors 11a and 11b.

While in FIG. 1 each circuit leg is provided with a single FET to enable the circuit leg to be switched in or switched out of the circuit, it is alternatively possible to provide two or more parallel-connected FETs in each circuit leg. The FETs of such an arrangement would all be switched on or switched off at the same time. The advantage of such an arrangement is that multiple FETs connected in parallel would further reduce any resistance values introduced by the individual FETs to further minimize heat losses in the circuitry. For example, in one embodiment it is desirable to keep the FET resistance below about 1 milli-ohm. This could be done, for example, by using a single FET having a resistance value of 0.8 milli-ohm when in the ON condition, or by using say 10 FETs in parallel, each with a resistance value of 8.0 milli-ohm. Thus, FETs or larger resistance values may still be employed. Of course, 10 FETs have a larger footprint than a single FET that may make them more susceptible to noise pick-up, so it is advisable to use FETs of smaller resistance values when they are available. By keeping the voltage of the ultra-capacitors low and the FET resistance low in the circuit legs, unwanted heat generation can be kept to a minimum, thereby making it possible to design measuring equipment having no need for heavy and bulky heat sinks, thus minimizing equipment size and weight and minimizing susceptibility of the equipment to pick-up external and internal electrical noise, thereby keeping the voltage signal "clean." If considered advantageous for particular applications, however, FETs 23a and 23b alone may be provided with heat sinks since they take the majority of the current flow and are in the ON condition all of the time during the measurement.

The activation of the various resistors in the two resistor ladder circuits can be in response to automatic monitoring of the current in real time via transducer 17 with appropriate generation of alerts to the FET controller 18. Suitable components to generate such alerts may be associated with the current meter A. An alternative approach is to pre-program the necessary operations into the FET controller 18 before a measurement operation is commenced so that the adjustments are made automatically according to an optimal time/resistance program established in advance for the circuit and the metal to be measured. Different metals may of course require different programs in view of their different resistance values and current flow characteristics.

To predetermine the sequence used to switch resistors on and off in the ladder for a particular metal, a calibration routine may be performed before actual measurement commences. According to such a routine, the ultra-capacitors $11a/11b$ are charged to a voltage that would provide greater than 65 amps when resistors $23a/23b$ are first turned on. This initial current may be around 70-80 amps. Then, resistors $23a/23b$ are turned on and, when the current decreases to about 65 amps, the voltage of the ultra-capacitors $11a$, $11b$ is recorded and is used to determine the ultra-capacitor charge voltage. When the current decreases to 60 amps, the remaining resistors are turned on in a binary coded sequence as indicated above until a current of 65 amps is once again established. The resistor binary state and ultra-cap voltage are recorded within controller 18 for the first transition. Each time the current decreases to 60 amps, the remaining resistors are turned on in the binary coded sequence until 65 amps is again achieved and the next transition binary state and ultra-cap voltage are recorded. This is done until all resistors in the ladders have been turned on and the current falls below 60 amps indicating the calibration is complete. During sampling, each effective transition state is set and recorded as stored calibration transition states. The recorded data from the calibration routine is employed by the controller 18 during a cleanliness measurement operation to issue the voltage signals via lines 20 to 70 to control the FETs to maintain the measurement current within the desired range. A time/resistance calibration operation may be carried out for each different molten metal or before every measurement if desired.

While the FETs are capable of switching their respective circuit legs on or off very rapidly, e.g. in a matter of microseconds, employing the binary sequence of operation as described, it is possible to discard any voltage measurements collected by voltage recorder V for the duration of the switching event as there will inevitable be a voltage jump when additional resistor(s) switch in or out and this may confuse the significance of the signal at that particular time. Thus, the voltage recorder V may be programmed, e.g. by a further micro-processor located within recorder V on an analog board (not shown), to automatically stop registering or recording of the voltage signal during a switching event as prompted by signals from the controller 18. Alternatively, the results from such switching periods, although recorded by recorder V, may simply be ignored by software during analysis of the voltage signal.

The voltage output recorded during a measurement period may be processed and analyzed to determine the number and characteristics of inclusions in the same manner as for conventional LiMCA devices. However, it is advantageous in some situations to analyze the signal in the manner described in co-pending U.S. provisional patent application Ser. No. 61/778,044 filed Mar. 12, 2013 and U.S. patent application Ser. No. 14/203,335, filed concurrently herewith, the entirety of which applications is incorporated herein by this reference. The features of the exemplary embodiments of the present application enable the device to avoid much external and internal electrical interference, so the resulting signal may be analyzed without the need for additional apparatus (e.g. further electrodes) or routines that may be required in the prior art, such as Marcotte et al. mentioned above. The exemplary embodiments may thus employ only two electrodes, i.e. electrodes $12a$ and $12b$ as shown. Having said this, it would of course be possible if desired in some particular applications to use the exemplary embodiments of the present invention with additional electrodes as described e.g. in the Marcotte et al. patent and to employ a similar method of signal analysis.

It is additionally useful to provide the exemplary embodiments with the ability to condition or purge the LiMCA probe prior to carrying out a measurement or auto calibration routine. This is done by delivering a very high current (e.g., 200-300 A or more) through the passage to displace or eliminate inclusions trapped in the passage or scale etc. lining the sides. This can be done by discharging the ultra-capacitors $11a$, $11b$ directly through the molten metal in the passage via a circuit having little or no electrical resistance, e.g. containing no ballast resistors. For this purpose, the ultra-capacitors may be connected in parallel (which is normal) or in series (when a higher current is required). Referring again to FIG. 1, these operations are controlled by FETs 25, 80, 90 and 100. With all other FETs turned off, turning on FETs 25, 80 and 90 causes the ultra-capacitors $11a$, $11b$ to discharge in parallel through the electrode $12a$. On the other hand, turning on FETs 80 and 100 with FET 25 turned off causes the ultra-capacitors to discharge in series. Control of these discharge FETs is maintained by voltages applied through lines 24, 26, 27 and 28 according to signals from controller 18. Line 24 controls FET 25, line 26 controls FET 80, line 27 controls FET 90, and line 28 controls FET 100. The current value during these discharges is determined by the resistance value of the metal between the electrodes plus current path impedances. The discharge can be selected with a duration lasting, for example, from 5 ms to 995 ms as required.

Figure 2:
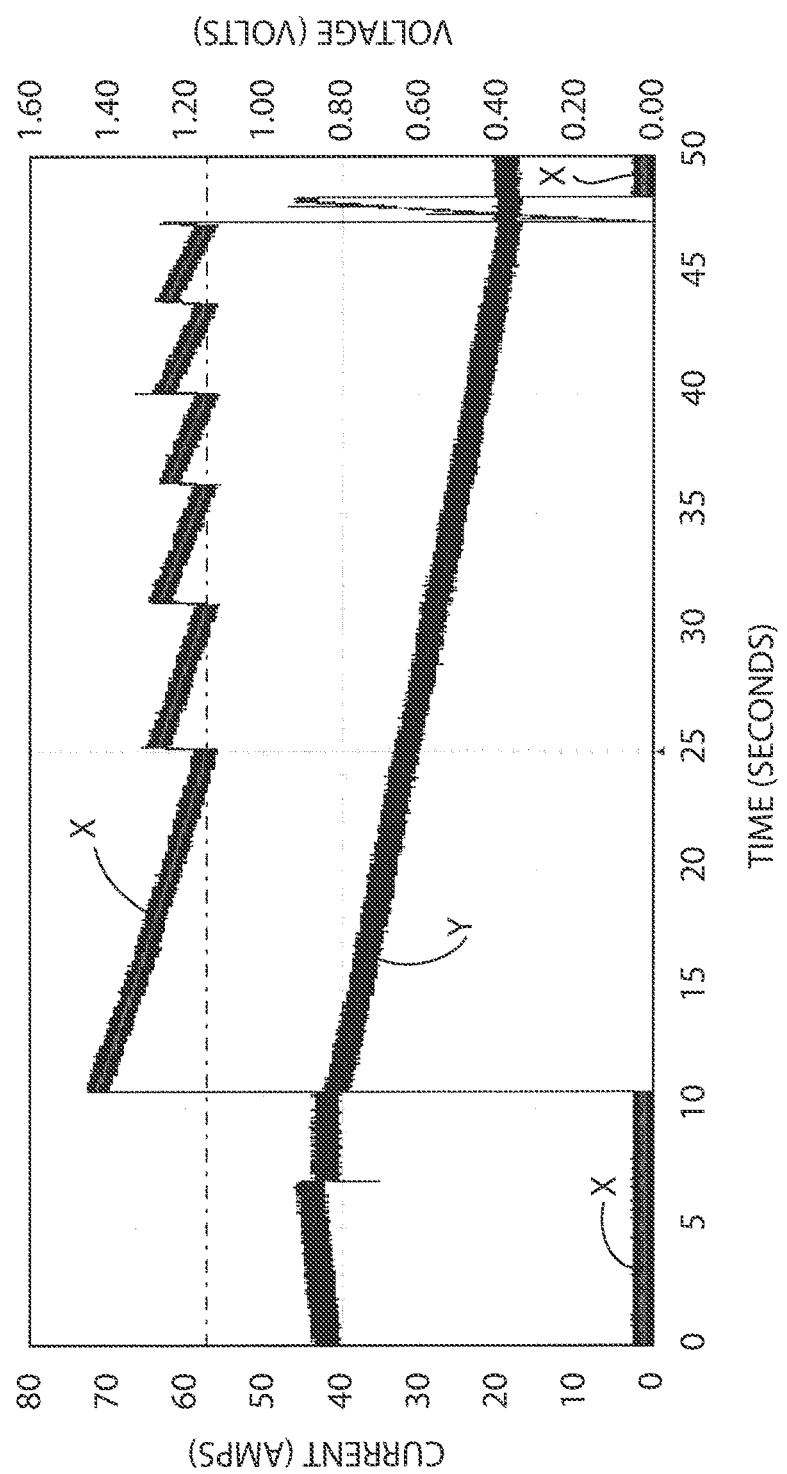
FIG. 2 is a chart showing the results of a test carried out according to an exemplary embodiment of the invention.

Apparatus of the above kind has been subjected to tests under real conditions in liquid aluminum in kilns at several test locations. Data saved during these tests included resistor states, discharge current, capacitor voltage, time, and many other parameters. The results of one of such tests are shown in FIG. 2 of the accompanying drawings, in which waveform X shows the measuring current in amps passing between the electrodes during the test period, and waveform Y shows the ultra-capacitor voltage as it discharges during the test period. It can be seen that, despite the decay of the discharge voltage of the ultra-capacitors, the current between the electrodes was maintained in the range of 58 to 63 amps.

This detailed description of the exemplary embodiments is used to illustrate the apparatus and method of the present invention. It will be clear to those skilled in the art that various modifications can be made thereto and that various alternative embodiments can be utilized without departing from the scope of the present invention, which is limited only by the appended claims.

What is claimed is:

1. Apparatus for measuring cleanliness of a molten metal, the apparatus comprising:
   one or more rechargeable ultra-capacitors operable at a discharge voltage of 2.7 volts or less;
   at least two electrodes;
   a metal cleanliness probe having an interior, a wall made of electrically resistive material and a passage in the wall interconnecting the interior with an exterior of the probe to allow molten metal to pass therethrough, wherein one of the at least two electrodes is positioned in the interior of the probe as an interior electrode and another of the at least two electrodes is positioned outside the probe as an exterior electrode;
   a device registering voltage across the interior and exterior electrodes and generating a voltage signal;

for each of the one or more ultra-capacitors, an associated resistor ladder network circuit interconnecting its associated ultra-capacitor with one of the electrodes, each resistor ladder network circuit comprising two or more resistors connected in parallel to each other, each resistor being in a circuit leg including one or more field effect transistors capable of being switched directly between a non-conductive OFF condition and a fully conductive ON condition, wherein each resistor ladder network circuit has resistance values effective to maintain a measurement current of no more than 100 amps through molten metal present in the passage when the circuit is exposed to the discharge voltage from the one or more ultra-capacitors;

a controller adapted for individually switching the field effect transistors of the circuit legs of each resistor ladder network circuit between the non-conductive OFF condition and the fully conductive ON condition according to a sequence effective for maintaining the measurement current within a pre-determined current range at least for a time required for measurement of cleanliness of the molten metal; and a switchable circuit by-passing each resistor ladder network circuit and connecting each ultra-capacitor directly across the interior and exterior electrodes for purging the passage.

2. The apparatus of claim 1, wherein the field effect transistor or transistors of each of the circuit legs are surface mounted field effect transistors.

3. The apparatus of claim 2, wherein the field effect transistor or transistors of each of the circuit legs introduce a resistance of less than 1 milli-ohm into the circuit leg when in the fully conductive ON condition.

4. The apparatus of claim 3, wherein at least one circuit leg includes two or more of the field effect transistors, and wherein the two or more field effect transistors are connected in parallel to each other.

5. The apparatus of claim 1, wherein the resistors of each resistor ladder network circuit have resistance values that differ from each other, and wherein the controller is programmed to switch the field effect transistors of the circuit legs to first turn on a circuit leg of lowest resistance, and then to turn on one or more circuit legs of higher resistance as the discharge voltage of the at least one ultra-capacitor declines during the time required for measurement.

6. The apparatus of claim 5, wherein each resistor ladder network circuit has three or more circuit legs and the controller is programmed to turn on the circuit legs according to a binary sequence effective to maintain the measurement current within the pre-determined current range.

7. The apparatus of claim 6, wherein the resistors each have a resistance value within a range of 0.02 to 2.64 ohms.

8. The apparatus of claim 1, further comprising a device measuring the measurement current and generating a signal alerting the controller when the current falls to a lower limit of the pre-determined current range.

9. The apparatus of claim 1, further comprising a voltage signal analyzer adapted to determine metal cleanliness from the signal from the device registering voltage.

10. The apparatus claim 1, further comprising a charger for charging the one or more of the rechargeable ultra-capacitors.

11. The apparatus of claim 1, having a single ultra-capacitor and a single associated resistor ladder network circuit.

12. The apparatus of claim 1, having two or more ultra-capacitors and two or more associated resistor ladder network circuits.

13. The apparatus of claim 12, wherein the switchable circuit is coupled to the two or more ultra-capacitors in series and by-passes the resistor ladder network circuits to connect the series-connected ultra-capacitors across the interior and exterior electrodes for purging the passage.

14. The apparatus of claim 1, wherein the at least two electrodes consist only of the internal electrode and the external electrode.

15. The apparatus of claims 1, wherein the one or more ultra-capacitors, the resistors and the field effect transistors are positioned on a circuit board immediately adjacent to each other to minimize susceptibility to noise reception.

16. A method of measuring cleanliness of a molten metal, the method comprising:

charging at least one ultra-capacitor to a voltage of 2.7 volts or less;

advancing molten metal through a passage in a wall made of electrically resistive material between an interior and an exterior of a metal cleanliness probe;

discharging the at least one ultra-capacitor, via a resistor ladder network circuit associated with each ultra-capacitor, through the molten metal advancing through the passage between an interior electrode positioned in the interior of the probe and an exterior electrode positioned outside the probe, wherein each resistor ladder network circuit comprises two or more resistors connected in parallel to each other, each resistor being in a circuit leg including one or more field effect transistors capable of being switched directly between a non-conductive OFF condition and a fully conductive ON condition, each resistor ladder network having resistance values effective to maintain a measurement current of no more than 100 amps through the molten metal advancing through the passage;

switching the field effect transistors of the circuit legs of each resistor ladder network circuit between the non-conductive OFF condition and the fully conductive ON condition according to a sequence for maintaining the measurement current within a pre-determined current range at least for a time required for measurement of cleanliness of the molten metal; and registering voltage across the internal and external electrodes during the time required for measurement, generating a voltage signal and determining cleanliness of the molten metal from the voltage signal, wherein the passage is purged before the time required for measurement of cleanliness of the molten metal by directing current from the at least one ultra-capacitor through molten metal in the passage while causing the current to by-pass each resistor ladder network circuit.

17. The method of claim 16, wherein each resistor ladder network circuit has three or more circuit legs and the individual switching of the field effect transistors of the circuit legs of each resistor ladder network ladder circuit is carried out according to a binary sequence to maintain the measurement current within the pre-determined current range.

18. The method of claim 16, wherein the sequence is pre-determined according to a calibration routine and recorded for use during the time required for measurement of cleanliness of the molten metal.

19. The method of claim 16, wherein the at least one ultra-capacitor is charged to a voltage of 0.8 to 1.4 volts.

20. The method of claim 16, wherein the field effect transistors are switched in each resistor ladder network circuit in a sequence to maintain the measurement current in a pre-determined range of 55 to 65 amps.

21. The method of claim 16, wherein the field effect transistors are switched in each resistor ladder network circuit in a sequence to maintain the measurement current in a predetermined range of 60 to 65 amps.

22. The method of claim 16, wherein the field effect transistors are switched from the OFF to the ON condition by voltage signals generated by a controller.

23. The method of claim 16, wherein charging at least one ultra-capacitor includes charging two ultra-capacitors, and wherein discharging the at least one ultra-capacitor includes discharging the two ultra-capacitors via two resistor ladder network circuits each associated with a respective one of the two ultra-capacitors.

24. The method of claim 23, wherein the passage is purged by connecting the two ultra-capacitors in series and discharging the series-connected ultra-capacitors through the passage.

* * * * *